US012097131B2

(12) United States Patent
Gill (10) Patent No.: US 12,097,131 B2
(45) Date of Patent: Sep. 24, 2024

(54) WRIST DEVICE FOR A PROSTHETIC LIMB

(71) Applicant: Touch Bionics Limited, Livingston (GB)

(72) Inventor: Hugh Gill, Paisley (GB)

(73) Assignee: Touch Bionics Limited, Livingston (GB)

( * ) Notice: Subject to any disclaimer, the term of this patent is extended or adjusted under 35 U.S.C. 154(b) by 232 days.

(21) Appl. No.: 17/664,783

(22) Filed: May 24, 2022

(65) Prior Publication Data
US 2022/0346978 A1 Nov. 3, 2022

Related U.S. Application Data

(63) Continuation of application No. 16/423,802, filed on May 28, 2019, now Pat. No. 11,357,646, which is a
(Continued)

(51) Int. Cl.
*A61F 2/58* (2006.01)
*A61F 2/70* (2006.01)
(Continued)

(52) U.S. Cl.
CPC .............. *A61F 2/585* (2013.01); *A61F 2/588* (2013.01); *A61F 2/70* (2013.01); *A61F 2/76* (2013.01);
(Continued)

(58) Field of Classification Search
CPC .......... A61F 5/0113; A61F 2/582; A61F 2/54; A61F 2/585; A61F 2/58; A61F 2/588;
(Continued)

(56) References Cited

U.S. PATENT DOCUMENTS

| 760,102 A | 5/1904 | Carnes |
| 1,253,823 A | 1/1918 | Hobbs |

(Continued)

FOREIGN PATENT DOCUMENTS

| CN | 1803413 | 7/2006 |
| CN | 106994694 | 8/2017 |

(Continued)

OTHER PUBLICATIONS

Michelangelo New Prosthetic Hand by Ottobock, Youtube. (Year: 2010).*

(Continued)

*Primary Examiner* — Christie Bahena
(74) *Attorney, Agent, or Firm* — Knobbe, Martens, Olson & Bear, LLP (57) ABSTRACT

A wrist device for a prosthetic limb is provided. The device (1) comprises a base member (3) connectable to the wearer of the device, and a support member (13) connectable to the limb. The support member (13) is pivotably connected to the base member (3) such that the support member can pivot about a pivot axis (A) relative to the base member. A damping mechanism is located between the base (3) member and the support member (5). The damping mechanism comprises a pinion (47) connected to the support member (5) and rotatable about the pivot axis (A) relative to the base member (3). A rack (35) is engaged with the pinion (47) such that rotational motion of the pinion causes a linear motion of the rack, and at least one biasing member (41) extends between the base member (3) and the rack. The biasing member (41) biases the rack (35) and support member (13) into a neutral position. A prosthetic limb incorporating the wrist device is also provided.

23 Claims, 5 Drawing Sheets

Related U.S. Application Data continuation of application No. 15/508,064, filed as application No. PCT/GB2015/052780 on Sep. 24, 2015, now Pat. No. 10,449,063.

(51) Int. Cl.
 *A61F 2/76* (2006.01)
 *A61F 2/50* (2006.01)
 *A61F 2/68* (2006.01)

(52) U.S. Cl.
 CPC ............... A61F 2002/5003 (2013.01); A61F 2002/5075 (2013.01); A61F 2002/6836 (2013.01); A61F 2002/6854 (2013.01); A61F 2002/6863 (2013.01)

(58) Field of Classification Search
 CPC ............... A61F 2/76; A61F 2002/543; A61F 2002/6854; A61F 2002/6863; Y10T 74/2042; Y10T 74/20552
 See application file for complete search history.

(56) References Cited

U.S. PATENT DOCUMENTS

| | | |
|---|---|---|
| 1,507,682 A | 9/1924 | Pecorella et al. |
| 1,507,683 A | 9/1924 | Pecorella et al. |
| 2,445,711 A | 7/1948 | Fitch |
| 2,477,463 A | 7/1949 | Otterman |
| 2,482,555 A | 9/1949 | Otterman |
| 2,508,156 A | 5/1950 | Gillman |
| 2,516,791 A * | 7/1950 | Motis ............... A61F 2/58 623/59 |
| 2,549,716 A | 4/1951 | Simpson |
| 2,586,293 A | 2/1952 | Birkigt |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraioli |
| 3,582,857 A | 6/1971 | Kishel |
| 3,641,832 A | 2/1972 | Shigeta et al. |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,094,016 A | 6/1978 | Eroyan |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A | 11/1986 | Childress et al. |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,775 A | 7/1992 | Chen |
| 5,246,463 A | 9/1993 | Giampapa |
| 5,252,102 A | 10/1993 | Singer et al. |
| 5,255,188 A | 10/1993 | Telepko |
| 5,387,245 A | 2/1995 | Fay et al. |
| 5,413,454 A | 5/1995 | Movsesian |
| 5,413,611 A | 5/1995 | Haslam, II et al. |
| 5,498,472 A | 3/1996 | Gold |
| 5,501,498 A | 3/1996 | Ulrich |
| 5,581,166 A | 12/1996 | Elsmann et al. |
| 5,605,071 A | 2/1997 | Buchanan, Jr. |
| 5,785,960 A | 7/1998 | Rigg et al. |
| 5,851,194 A | 12/1998 | Fratrick |
| 5,852,675 A | 12/1998 | Matsuo et al. |
| 5,888,213 A | 3/1999 | Sears et al. |
| 5,888,246 A | 3/1999 | Gow |
| 5,900,714 A | 5/1999 | Dubhashi et al. |
| 6,111,973 A | 8/2000 | Holt et al. |
| 6,175,962 B1 | 1/2001 | Michelson |
| 6,223,615 B1 | 5/2001 | Huck |
| 6,244,873 B1 | 6/2001 | Hill et al. |
| 6,344,062 B1 | 2/2002 | Abboudi et al. |
| 6,361,570 B1 | 3/2002 | Gow |
| 6,591,707 B2 | 7/2003 | Torii et al. |
| 6,660,043 B2 | 12/2003 | Kajitani et al. |
| 6,786,112 B2 | 9/2004 | Ruttor |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,640,680 B1 | 1/2010 | Castro |
| 7,823,475 B2 | 11/2010 | Hirabayashi et al. |
| 7,867,287 B2 | 1/2011 | Puchhammer |
| 7,922,773 B1 | 4/2011 | Kuiken |
| 8,016,893 B2 | 9/2011 | Weinberg et al. |
| 8,100,986 B2 | 1/2012 | Puchhammer et al. |
| 8,197,554 B2 | 6/2012 | Whiteley et al. |
| 8,257,446 B2 | 9/2012 | Puchhammer |
| 8,337,568 B2 | 12/2012 | Macduff |
| 8,491,666 B2 | 7/2013 | Schulz |
| 8,579,991 B2 | 11/2013 | Puchhammer |
| 8,593,255 B2 | 11/2013 | Pang et al. |
| 8,657,887 B2 | 2/2014 | Gill |
| 8,662,552 B2 | 3/2014 | Torres-Jara |
| 8,663,339 B2 | 3/2014 | Inschlag et al. |
| 8,690,963 B2 | 4/2014 | Puchhammer |
| 8,696,763 B2 | 4/2014 | Gill |
| 8,739,315 B2 | 6/2014 | Baacke |
| 8,803,844 B1 | 8/2014 | Green et al. |
| 8,808,397 B2 | 8/2014 | Gow |
| 8,828,096 B2 | 9/2014 | Gill |
| 8,986,395 B2 | 3/2015 | McLeary |
| 8,995,760 B2 | 3/2015 | Gill |
| 9,278,012 B2 | 3/2016 | Gill |
| 9,333,096 B2 | 5/2016 | Perez de Alderete et al. |
| 9,387,095 B2 | 7/2016 | McLeary et al. |
| 9,402,749 B2 | 8/2016 | Gill et al. |
| 9,435,400 B2 | 9/2016 | Cheung et al. |
| 9,463,100 B2 | 10/2016 | Gill |
| 9,707,103 B2 | 7/2017 | Thompson, Jr. et al. |
| 9,720,515 B2 | 8/2017 | Wagner et al. |
| 9,839,534 B2 | 12/2017 | Lipsey et al. |
| 9,999,522 B2 | 6/2018 | Gill |
| 10,047,908 B1 | 8/2018 | Bohle, II et al. |
| 10,265,197 B2 | 4/2019 | Gill et al. |
| 10,318,863 B2 | 8/2019 | Lock et al. |
| 10,369,016 B2 | 8/2019 | Lipsey et al. |
| 10,369,024 B2 | 8/2019 | Gill |
| 10,398,576 B2 | 9/2019 | Gill et al. |
| 10,449,063 B2 | 10/2019 | Gill |
| 10,610,385 B2 | 4/2020 | Meljer et al. |
| 11,185,426 B2 | 11/2021 | Gill et al. |
| 11,357,646 B2 | 6/2022 | Gill |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2004/0002672 A1 | 1/2004 | Carlson |
| 2004/0054423 A1 | 3/2004 | Martin |
| 2004/0078091 A1 | 4/2004 | Elkins |
| 2004/0078299 A1 | 4/2004 | Down-Logan et al. |
| 2004/0103740 A1 | 6/2004 | Townsend et al. |
| 2004/0181289 A1 | 9/2004 | Bedard et al. |
| 2004/0182125 A1 | 9/2004 | McLean |
| 2005/0021154 A1 | 1/2005 | Brimalm |
| 2005/0021155 A1 | 1/2005 | Brimalm |

(56) References Cited

U.S. PATENT DOCUMENTS

| | | |
|---|---|---|
| 2005/0093997 A1 | 5/2005 | Dalton et al. |
| 2005/0101693 A1 | 5/2005 | Arbogast et al. |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0102228 A1 | 5/2007 | Shiina et al. |
| 2007/0137351 A1 | 6/2007 | Schwendemann |
| 2007/0173955 A1* | 7/2007 | Archer .............. A61F 2/585 623/61 |
| 2007/0175681 A1 | 8/2007 | King et al. |
| 2007/0230832 A1 | 10/2007 | Usui et al. |
| 2007/0260328 A1* | 11/2007 | Bertels .............. A61F 2/70 623/59 |
| 2007/0276303 A1 | 11/2007 | Jenner, Jr. |
| 2008/0058668 A1 | 3/2008 | Seyed Momen et al. |
| 2008/0097269 A1 | 4/2008 | Weinberg et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0213379 A1 | 8/2009 | Carroll et al. |
| 2010/0016990 A1 | 1/2010 | Kurtz |
| 2010/0116078 A1 | 5/2010 | Kim |
| 2010/0274365 A1 | 10/2010 | Evans et al. |
| 2011/0048098 A1 | 3/2011 | Rollins et al. |
| 2011/0136376 A1* | 6/2011 | Johnson .............. B25J 15/04 439/529 |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Fillol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0109337 A1 | 5/2012 | Schulz |
| 2012/0204665 A1 | 8/2012 | Baudasse |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330439 A1 | 12/2012 | Goldfarb et al. |
| 2013/0041476 A1 | 2/2013 | Schulz |
| 2013/0053984 A1 | 2/2013 | Hunter et al. |
| 2013/0059467 A1 | 3/2013 | Johnson et al. |
| 2013/0076699 A1 | 3/2013 | Spencer |
| 2013/0144197 A1 | 6/2013 | Ingimundarson et al. |
| 2013/0175816 A1 | 7/2013 | Kawasaki et al. |
| 2013/0253705 A1 | 9/2013 | Goldfarb et al. |
| 2013/0268090 A1 | 10/2013 | Goldfarb et al. |
| 2013/0268094 A1 | 10/2013 | Van Wiemeersch |
| 2013/0310949 A1 | 11/2013 | Goldfarb et al. |
| 2014/0236314 A1 | 8/2014 | Van Wiemeersch |
| 2014/0251056 A1 | 9/2014 | Preuss |
| 2014/0324189 A1 | 10/2014 | Gill et al. |
| 2014/0371871 A1 | 12/2014 | Farina et al. |
| 2015/0142082 A1 | 5/2015 | Simon et al. |
| 2015/0183069 A1 | 7/2015 | Lee |
| 2015/0216681 A1 | 8/2015 | Lipsey et al. |
| 2015/0230941 A1 | 8/2015 | Jury |
| 2015/0351935 A1 | 12/2015 | Donati et al. |
| 2015/0360369 A1 | 12/2015 | Ishikawa et al. |
| 2015/0374515 A1 | 12/2015 | Meijer et al. |
| 2016/0250044 A1 | 9/2016 | Iversen et al. |
| 2016/0287422 A1 | 10/2016 | Kelly et al. |
| 2017/0007424 A1 | 1/2017 | Gill |
| 2017/0049586 A1 | 2/2017 | Gill et al. |
| 2018/0064563 A1 | 3/2018 | Gill |
| 2018/0071115 A1 | 3/2018 | Lipsey et al. |
| 2018/0168830 A1 | 6/2018 | Evans et al. |
| 2018/0296368 A1 | 10/2018 | Gill |
| 2019/0091040 A1 | 3/2019 | Gill |
| 2019/0183661 A1 | 6/2019 | Gill |
| 2019/0209345 A1 | 7/2019 | LaChappelle |
| 2019/0216618 A1 | 7/2019 | Gill |
| 2019/0375067 A1 | 12/2019 | Berrocal et al. |
| 2019/0380846 A1 | 12/2019 | Lipsey et al. |
| 2020/0054466 A1 | 2/2020 | Gill et al. |
| 2020/0197193 A1 | 6/2020 | Byrne et al. |
| 2022/0151805 A1 | 5/2022 | Gill et al. |

FOREIGN PATENT DOCUMENTS

| | | |
|---|---|---|
| DE | 309 367 | 11/1918 |
| DE | 24 34 834 | 2/1976 |
| DE | 198 54 762 | 6/2000 |
| DE | 101 05 814 | 9/2002 |
| DE | 203 15 575 | 1/2004 |
| DE | 698 16 848 | 4/2004 |
| DE | 10 2012 009 699 | 11/2013 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 1 557 547 | 1/2011 |
| EP | 2 532 927 | 12/2012 |
| EP | 2 612 619 | 7/2013 |
| EP | 2 653 137 | 10/2013 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 278 281 | 11/1994 |
| GB | 2 357 725 A | 7/2001 |
| GB | D 3023680 | 4/2006 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| JP | 2018-167375 | 11/2018 |
| WO | WO 95/024875 | 9/1995 |
| WO | WO 96/023643 | 8/1996 |
| WO | WO 99/021517 | 5/1999 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |

(56) References Cited

FOREIGN PATENT DOCUMENTS

| | | |
|---|---|---|
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2014/027897 | 2/2014 |
| WO | WO 2015/120076 | 8/2015 |
| WO | WO 2015/120083 | 8/2015 |
| WO | WO 2016/051138 | 4/2016 |
| WO | WO 2017/061879 | 4/2017 |
| WO | WO 2018/180782 | 10/2018 |
| WO | WO 2021/177840 | 9/2021 |

OTHER PUBLICATIONS

9 Worm Gear Pair, KHK Technical Information, Oct. 21, 2008, pp. 291-299.

Albu-Schaffer et al., "Soft Robotics", IEEE Robotics & Automation Magazine, Sep. 2008, vol. 15, No. 3, pp. 20-30.

AMA, Excerpts from American Medical Association, Guides to the Evaluation of Permanent Impairment (5th ed. 2000), pp. 432-453.

Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.

Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.

Belter et al., "Mechanical Design and Performance Specifications of Anthropomorphic Prosthetic Hands: A Review", JRRD, Nov. 5, 2013, vol. 50, No. 5, pp. 599-617.

Biddiss et al., "Consumer Design Priorities for Upper Limb Prosthetics", Disability and Rehabilitation: Assistive Technology, Nov. 2007, vol. 2, No. 6, pp. 346-357.

Biddiss et al., "Upper Limb Prosthesis Use and Abandonment: A Survey of the Last 25 Years", Prosthetics and Orthotics International, Sep. 2007, vol. 31, No. 3, pp. 236-257.

Biddiss et al., "Upper-Limb Prosthetics: Critical Factors in Device Abandonment", American Journal of Physical Medicine & Rehabilitation, Dec. 2007, vol. 86, No. 12, pp. 977-987.

Bretthauer et al., "A New Adaptive Hand Prosthesis", Handchirurgie Mikrochirurgie Plastische Chirurgie, Feb. 2008, pp. 40-45.

Butterfaß et al., "DLR-Hand II: Next Generation of a Dextrous Robot Hand", IEEE International Conference on Robotics and Automation, Seoul, Korea, May 21-26, 2001, vol. 1, pp. 109-114.

Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.

Childress et al., "Control of Limb Prostheses", American Academy of Orthopaedic Surgeons, Mar. 2004, Chapter 12, pp. 173-195.

Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.

Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.

Connolly, "Prosthetic Hands from Touch Bionics", Industrial Robot, Emerald Group Publishing Limited, Jun. 2008, vol. 35, No. 4, pp. 290-293.

Controzzi et al., "Miniaturized Non-Back-Drivable Mechanism for Robotic Applications", Mechanism and Machine Theory, Oct. 2010, vol. 45, No. 10, pp. 1395-1406.

Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.

"DC Circuit Theory", <https://www.electronics-tutorials.ws/dccircuits/dcp_1.html>, Date verified by the Wayback Machine Apr. 23, 2013, pp. 16.

Dechev et al., "Multiple Finger, Passive Adaptive Grasp Prosthetic Hand", Mechanism and Machine Theory, Oct. 1, 2001, vol. 36, No. 10, pp. 1157-1173.

Dellorto, Danielle, "Bionic Hands Controlled by iPhone App", CNN, Apr. 12, 2013, pp. 4 <http://www.cnn.com/2013/04/12/health/bionic-hands>.

"DuPont Engineering Design—The Review of DuPont Engineering Polymers in Action"; <http://www.engpolymer.co.kr/x_data/magazine/engdesign07_2e.pdf>, Feb. 2007, pp. 16.

Edsinger-Gonzales, Aaron, "Design of a Compliant and Force Sensing Hand for a Humanoid Robot", 2005, pp. 5.

Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.

Fildes, Jonathan, "Bionic Hand Wins Top Tech Prize", BBC News, Jun. 9, 2008, http://news.bbc.co.uk/2/hi/science/nature/7443866.stm, pp. 3.

Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.

Fukuda et al., "Training of Grasping Motion Using a Virtual Prosthetic Control System", 2010 IEEE International Conference on Systems Man and Cybernetics (SMC), Oct. 10-13, 2010, pp. 1793-1798.

Gaine et al., "Upper Limb Traumatic Amputees. Review of Prosthetic Use", The Journal of Hand Surgery, Feb. 1997, vol. 22B, No. 1, pp. 73-76.

Grip Chips™, Datasheet, May 15, 2014, Issue 1, <http://touchbionics.com/sites/default/files/files/Grip%20Chip%20datasheet%20May%202014.pdf>, pp. 1.

Heckathorne, Craig W., "Components for Electric-Powered Systems", American Academy of Orthopaedic Surgeons, Mar. 2004, Chapter 11, pp. 145-171.

Hojjat et al., "A Comprehensive Study on Capabilities and Limitations of Roller-Screw with Emphasis on Slip Tendency", Mechanism and Machine Theory, Oct. 2009, vol. 44, No. 10, pp. 1887-1899.

Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.

"ILimb Bionic Hand Now Ready for Market", Technovelgy.com, www.technovelgy.com/ct/Science-Fiction-News.asp?NewsNum=1125, as printed Jul. 6, 2020 in 3 pages.

Jebsen et al., "An Objective and Standardized Test of Hand Function", Archives of Physical Medicine and Rehabilitation, Jun. 1969, vol. 50, No. 6, pp. 311-319.

Johannes et al., "An Overview of the Developmental Process for the Modular Prosthetic Limb," John Hopkins APL Technical Digest, 2011, vol. 30, No. 3, pp. 207-216.

Kargov et al., "Applications of a Fluidic Artificial Hand in the Field of Rehabilitation", Rehabilitation Robotics, Ch. 15, Aug. 2007, pp. 261-286.

(56) References Cited

OTHER PUBLICATIONS

Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.
Kawasaki et al., "Design and Control of Five-Fingered Haptic Interface Opposite to Human Hand", IEEE Transactions on Robotics, Oct. 2007, vol. 23, No. 5., pp. 909-918.
Kent et al., "Electromyogram Synergy Control of a Dexterous Artificial Hand to Unscrew and Screw Objects", Journal of Neuroengineering and Rehabilitation, Mar. 2014, vol. 11, No. 1, pp. 1-20.
Kermani et al., "Friction Identification and Compensation in Robotic Manipulators", IEEE Transactions on Instrumentation and Measurement, Dec. 2007, vol. 56, No. 6, pp. 2346-2353.
Kuiken et al., "Targeted Muscle Reinnervation for Real-Time Myoelectric Control of Multifunction Artificial Arms", JAMA, Feb. 11, 2009, vol. 301, No. 6, pp. 619-628.
Kyberd et al., "Two-Degree-of-Freedom Powered Prosthetic Wrist", Journal of Rehabilitation Research & Development, Jul. 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.
Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.
Majd et al., "A Continuous Friction Model for Servo Systems with Stiction", in Proceedings of the IEEE Conference on Control Applications, Sep. 28-29, 1995, pp. 296-301.
Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.
Maxon Precision Motors, Inc., "Maxon Flat Motor: EX 10 flat 10 mm, brushless, 0.25 Watt", Specification, May 2011, p. 181.
Maxon Precision Motors, Inc., "Maxon EC Motor: EC10 10 mm, brushless, 8 Watt", Specification, May 2011, p. 140.
MEC '05: Integrating Prosthetics and Medicine, University of New Brunswick's MyoElectric Controls/Powered Prosthetics Symposium, Aug. 17-19, 2005, Fredericton NB Canada, p. 260.
Miller et al., "Summary and Recommendations of the Academy's State of the Science Conference on Upper Limb Prosthetic Outcome Measures", Journal of Prosthetics Orthotics, Oct. 2009, vol. 21, pp. 83-89.
Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.
Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.
"Motor Technology—Girard Gearboxes Low Backlash Principle Explained", Motor Technology, https://www.motec.co.uk/tip-gearbox_principle.htm as printed May 23, 2012 in 3 pages.
Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.
Osborn et al., "Utilizing Tactile Feedback for Biomimetic Grasping Control in Upper Limb Prostheses", Department of Biomedical Engineering, Johns Hopkins University, Baltimore, USA, Nov. 5, 2013, pp. 4.

Pedrocchi et al., "MUNDUS Project: Multimodal Neuroprosthesis for Daily Upper Limb Support", Journal of Neuroengineering and Rehabilitation, Jul. 2013, vol. 10, No. 66, pp. 20.
Pinzur et al., "Functional Outcome Following Traumatic Upper Limb Amputation and Prosthetic Limb Fitting", The Journal of Hand Surgery, Sep. 1994. vol. 19, pp. 836-839.
Poppe, Zytel HTN Provides a Helping Hand, DuPont Engineering Design 8 (2007), pp. 3.
Press Release, "Touch Bionics Introduce Digitally Controlled Supro Wrist", <http://www.touchbionics.com/news-events/news/touch-bionics-introduce-digitally-controlled-supro-wrist>, May 3, 2016 in 2 pages.
Puig et al., "A Methodology for the Design of Robotic Hands with Multiple Fingers", International Journal of Advanced Robotic Systems, 2008, vol. 5, No. 2, pp. 177-184.
Raspopovic et al., "Restoring Natural Sensory Feedback in Real-Time Bidirectional Hand Prostheses", Science Translational Medicine, Feb. 5, 2014, vol. 6, No. 222, pp. 1-10.
Resnik et al., "The DEKA Arm: Its Features, Functionality, and Evolution During the Veterans Affairs Study to Optimize the DEKA Arm", Prosthetics and Orthotics International, Oct. 2013, vol. 38, No. 6, pp. 492-504.
Scheme et al., "Electromyogram Pattern Recognition for Control of Powered Upper-Limb Prostheses: State of the Art and Challenges for Clinical Use", Journal of Rehabilitation Research & Development (JRRD), Jul. 2011, vol. 48, No. 6, pp. 643-659.
Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.
Schulz et al., "Die Entwicklung Einer Multifunktionalen Kosmetischen Handprothese", Prothetik, Orthopädie-Technik, Aug. 2006, pp. 627-632.
Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.
Sensinger, "Efficiency of High-Sensitivity Gear Trains, such as Cycloid Drives", Journal of Mechanical Design, Jul. 2013, vol. 135, No. 7, pp. 071006-1-071006-9.
Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.
Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.
Stix, Gary, "Phantom Touch: Imbuing a Prosthesis with Manual Dexterity", Scientific American, Oct. 1998, pp. 41 & 44.
"Supro Wrist", Touch Bionics, <https://web.archive.org/web/20160928141440/http://www.touchbionics.com/products/supro-wrist> as archived Sep. 28, 2016 in 3 pages.
Sutton et al., "Towards a Universal Coupler Design for Modern Powered Prostheses", MEC 11 Raising the Standard, Proceedings of the 2011 MyoElectric Controls/Powered Prosthetics Symposium Fredericton, New Brunswick, Canada, Aug. 14-19, 2011, pp. 5.
Tan et al., "A Neural Interface Provides Long-Term Stable Natural Touch Perception", Science Translational Medicine, Oct. 8, 2014, vol. 6, No. 257, pp. 1-11.
Tang, "General Concepts of Wrist Biomechanics and a View from Other Species", The Journal of Hand Surgery, European Volume, Aug. 2008, vol. 33, No. 4, pp. 519-525.

(56) References Cited

OTHER PUBLICATIONS

The Weir Thesis ("Weir Thesis") is entitled "An Externally-Powered, Myo-Electrically Controlled Synergetic Prosthetic Hand for the Partial-Hand Amputee", published Aug. 1989, pp. 365. [Uploaded in 3 Parts].
Toledo et al., "A Comparison of Direct and Pattern Recognition Control for a Two Degree-of-Freedom Above Elbow Virtual Prosthesis", in Proceedings 34th Annual International Conference of the IEEE EMBS, Aug. 2012, pp. 4332-4335.
"Touch Bionics Grip Chips Let Hand Prostheses Think for Themselves", May 15, 2014, <www.medgadget.com/2014/05/touch-bionics-grip-chips-let-hand-prostheses-think-for-themselves.html>, pp. 2.
Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint Slide in 1 page, believed to be presented at Advanced Arm Dynamics company Jan. 11, 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.
Vilarino, Martin, "A Novel Wireless Controller for Switching among Modes for an Upper-Limb Prosthesis", The Academy Today, Jan. 2014, vol. 10, No. 1, pp. A-12 to A-15.
Ward, Derek Kempton, "Design of a Two Degree of Freedom Robotic Finger", Sep. 1996, in 155 pages.
Weir et al., "Design of Artificial Arms and Hands for Prosthetic Applications", Biomedical Engineering and Design Handbook, Jul. 2009, vol. 2, pp. 537-598.
Wettels et al., "Grip Control Using Biomimetic Tactile Sensing Systems", IEEE/ASME Transactions on Mechatronics, Dec. 2009, vol. 14, No. 6, pp. 718-723.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.
Zampagni et al., "A Protocol for Clinical Evaluation of the Carrying Angle of the Elbow by Anatomic Landmarks", Journal of Shoulder and Elbow Surgery, Jan. 1, 2008, vol. 17, No. 1, pp. 106-112.
International Search Report and Written Opinion in Application No. PCT/GB2015/052780, mailed Jan. 7, 2016.
International Preliminary Report on Patentability and Written Opinion in Application No. PCT/GB2015/052780, mailed Apr. 13, 2017.

\* cited by examiner

WRIST DEVICE FOR A PROSTHETIC LIMB

FIELD OF THE INVENTION

The present invention relates to the field prosthetic limbs. More specifically, the present invention is a wrist device which allows a prosthetic limb to be manipulated relative to the wearer of the limb.

BACKGROUND OF THE INVENTION

Wrist devices for the manipulation of prosthetic limbs are known. In such devices, a prosthetic limb such as a prosthetic hand or digit is fixed to a support member which is pivobuttonly coupled to a base member. The base member is attached to a socket located on the wearer's residual limb or stump. The support member and hand can pivot relative to the base member in order to move the hand/digit into different positions.

An example of one such device is disclosed in US2007/0260328, in which a prosthetic hand and support member can pivot in a flexion/extension plane relative to a base member. A gear segment attached to the support member has a number of indentations which are engaged by resilient retention elements which hold the support member and hand in certain positions relative to the base member. The wearer pulls or pushes the prosthetic hand in the flexion/extension plane in order to move the hand to a new position. As this takes place the retention elements are forced out of their current indentations in the gear segment and will enter the adjacent indentations as the gear segment rotates. In addition to the retention elements a sliding locking device can be slid in and out of engagement with slots in the gear segment in order to lock the hand in a particular position. The locking device is biased into a locked position by a spring.

A similar arrangement is disclosed in U.S. Pat. No. 7,144,430, which also discloses an arrangement in which the hand and support member can be manipulated in both the flexion/extension and adduction/abduction directions about a form of universal joint. Torsion springs are provided which bias the hand into a neutral position. One or more spring-loaded locking pins engage the hand to lock it into positions along one or both of the flexion/extension and adduction/abduction axes.

In arrangements such as those referred to above, the prosthesis wearer can find it difficult to overcome the biasing forces of the resilient members or springs which hold the hand in position or force the hand towards a given position. Consequently, repeated movements of the hand about the wrist device can lead to fatigue in the wearer. In addition, the biased locking arrangements which lock the hand in a given position can be cumbersome and awkward for a wearer to actuate with their remaining natural hand, and even more so if they have another hand prosthesis.

It is an object of the present invention to obviate or mitigate one or more of these disadvantages.

SUMMARY OF THE INVENTION

According to a first aspect of the invention, there is provided wrist device for a prosthetic limb, the device comprising:
- a base member connectable to the wearer of the device;
- a support member connectable to the limb, the support member being pivotably connected to the base member such that the support member can pivot about a pivot axis relative to the base member; and
- a damping mechanism located between the base member and the support member, the damping mechanism comprising:
  - a pinion connected to the support member and rotatable about the pivot axis relative to the base member;
  - a rack engaged with the pinion such that rotational motion of the pinion causes a linear motion of the rack; and
  - at least one biasing member extending between the base member and the rack, the biasing member biasing the rack and support member into a neutral position.

The device may comprise first and second biasing members, with each of the first and second biasing members extending between the base member and the rack and biasing the rack and support member into the neutral position from substantially opposite directions.

The first and second biasing members may comprise first and second compression springs located between the rack and the base member, wherein the first spring biases the rack in a first direction and the second spring biases the rack in a substantially opposite second direction.

The compression springs may be partially housed within the rack, wherein a first end of each spring is engaged with an internal surface of the rack and a second end of each spring is engaged with the base member.

The base member may be provided with first and second adjustment members which can adjust the biasing force of the first and second springs, respectively.

The device may further comprise a locking mechanism for selectively preventing movement of the support member relative to the base member, the locking mechanism comprising an actuator which is moveable between locked and unlocked positions, the actuator including a first locking element which prevents movement of the pinion when the actuator is in the locked position.

The actuator may comprise an actuator shaft extending through the pinion along the pivot axis, and first and second actuator buttons at opposite ends of the shaft, wherein the actuator can move axially along the pivot axis relative to the base member and pinion when the first or second button is pressed, one of the first and second buttons incorporating the first locking element.

The device may further comprise a pinion shaft which is rotatably supported on the base member and rotatably coupled to the pinion, wherein the pinion shaft has a second locking element at one end thereof, the first and second locking elements engaging to prevent rotation of the pinion when the actuator is in the locked position.

The button which incorporates the first locking element may have a bottom surface which engages an upper surface of the base member when the actuator is in the locked position, thereby preventing relative rotation between the actuator and the base member.

At least one of the base member and actuator may include one or more magnets, the or each magnet attracting the actuator towards the locked or unlocked position when the actuator is within a predetermined distance of the base member.

The base member and first and second actuator buttons may include magnets such that each button is attracted to the base member when it comes within a predetermined distance of the base member.

The locking mechanism may further comprise a cover member having an opening through which the support member extends, the cover member enclosing the locking mechanism and engaging the first and second actuator buttons such that axial movement of the cover member will result in a corresponding movement of the actuator.

The device may further comprise at least one flexible covering located between the pinion and the opening in the cover member so as to prevent ingress of contaminants into the device.

The base member may include a quick release coupling for connecting the device to the wearer.

According to a second aspect of the invention there is provided a prosthetic limb comprising a wrist device according to the first aspect of the invention.

BRIEF DESCRIPTION OF THE DRAWINGS

A preferred embodiment of the present invention will now be described, by way of example only, with reference to the following drawings.

DETAILED DESCRIPTION OF THE DRAWINGS

Figure 1:
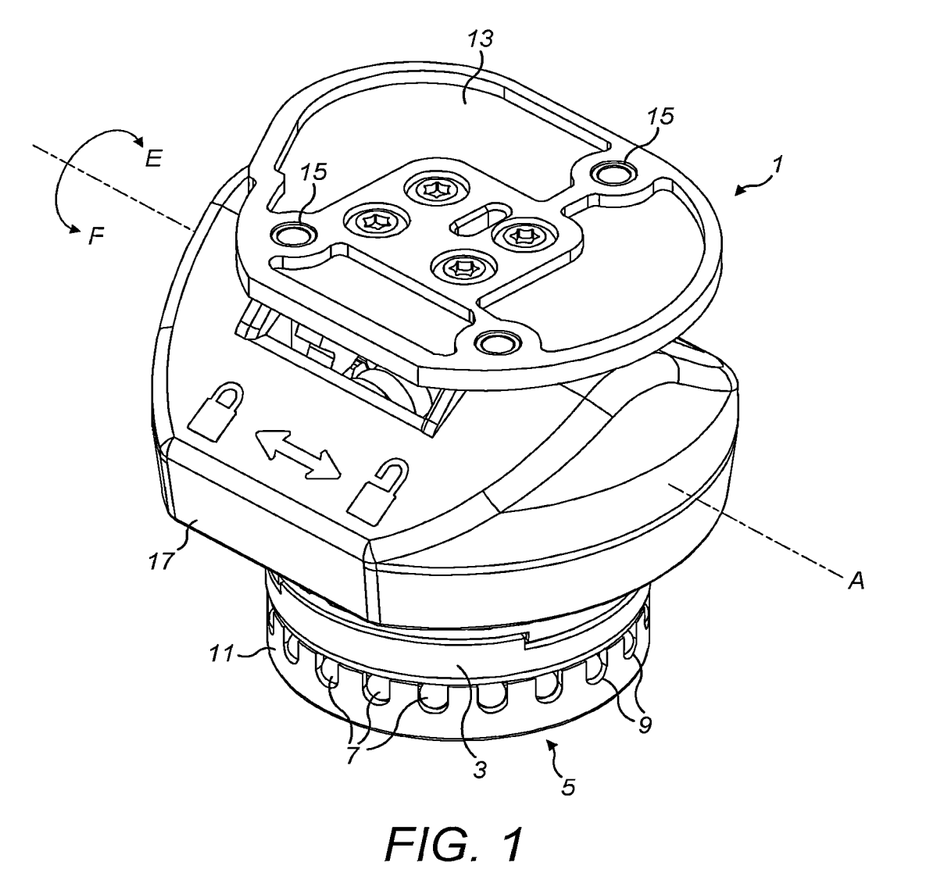
FIG. 1 is a perspective view of a wrist device for a prosthetic limb.

FIG. 1 shows a wrist device 1 for a prosthetic limb (not shown), which may be a prosthetic hand, for example. The wrist device 1 comprises a base 3, which is provided with attachment means for attaching the base 3 to a socket (not shown) on a patient's residual limb or stump. In the illustrated embodiment, the attachment means is a quick release connection in the form of a spring-loaded ball bearing arrangement 5, in which a plurality of ball bearings 7 are circumferentially arranged around the outer surface of the base 3. The ball bearings 7 are biased radially outwards by biasing means (not shown) so that each ball 7 is partially exposed through apertures 9 in a retaining ring 11 which sits on the outer surface of the base 3. The socket has an equivalent female recess with a plurality of indentations corresponding to the number of ball bearings 7. Consequently, as the base 3 is inserted into the female recess in the socket the ball bearings 7 are pressed radially inwards against the force of the biasing means, and when the ball bearings 7 meet the indentations of the socket they are pressed radially outwards by the biasing means in order to locate in the indentations. In this manner, the base 3 will be connected to the socket until such time are the wearer applies sufficient force to the base by twisting and/or pulling in order to overcome the force of the biasing means and disconnect the base 3 from the socket.

A support member, or plate, 13 is pivotably connected to the base 3 so that the plate 13 may pivot about a pivot axis A relative to the base 3. The plate 13 is provided with a number of apertures 15 which allow the prosthetic limb to be attached to the plate 13. Pivoting about the pivot axis A permits the plate 13 to move in directions which replicate flexion and extension movements of a natural wrist relative to the forearm. These respective movements are illustrated by arrowheads F and E in FIG. 1.

The device 1 further comprises a locking mechanism which the wearer can actuate in order to selectively lock the plate 13 in a particular position relative to the base 3. The only component of the locking mechanism which is visible in FIG. 1 is a cover member 17 which can be moved axially along the axis A between positions which correspond with locked and unlocked states of the locking mechanism. Further details of the locking mechanism and the manner in which it operates will be described in more detail below.

Figure 2:
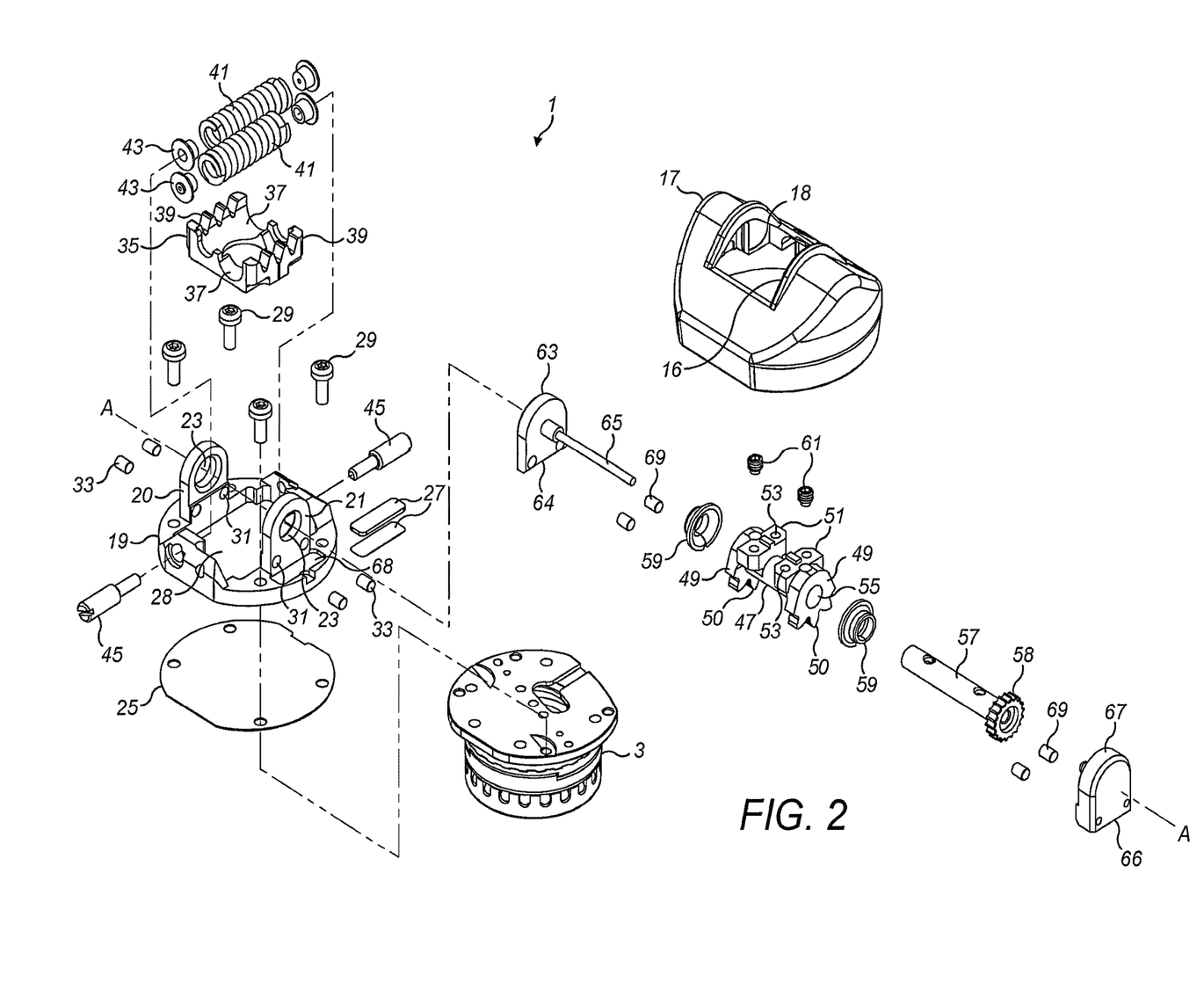
FIG. 2 is an exploded view of the device shown in FIG. 1.
Figure 4:
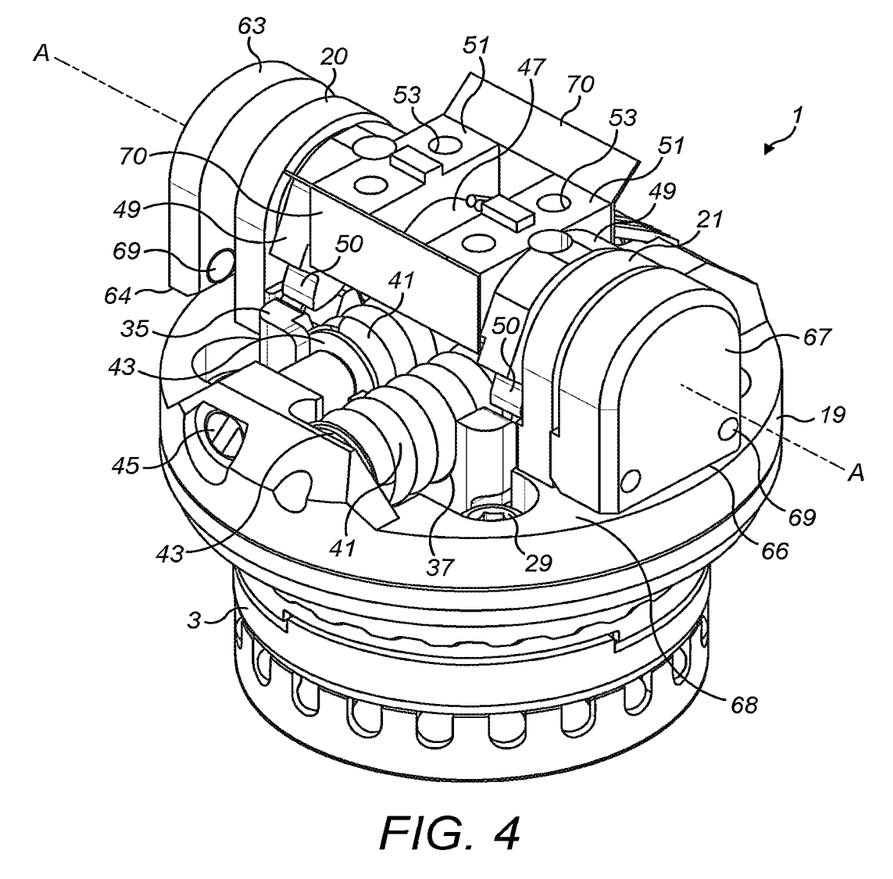
FIGS. 4 and 5 are perspective and top views respectively of the device of FIG. 1 with certain components removed for illustrative purposes.
Figure 5:
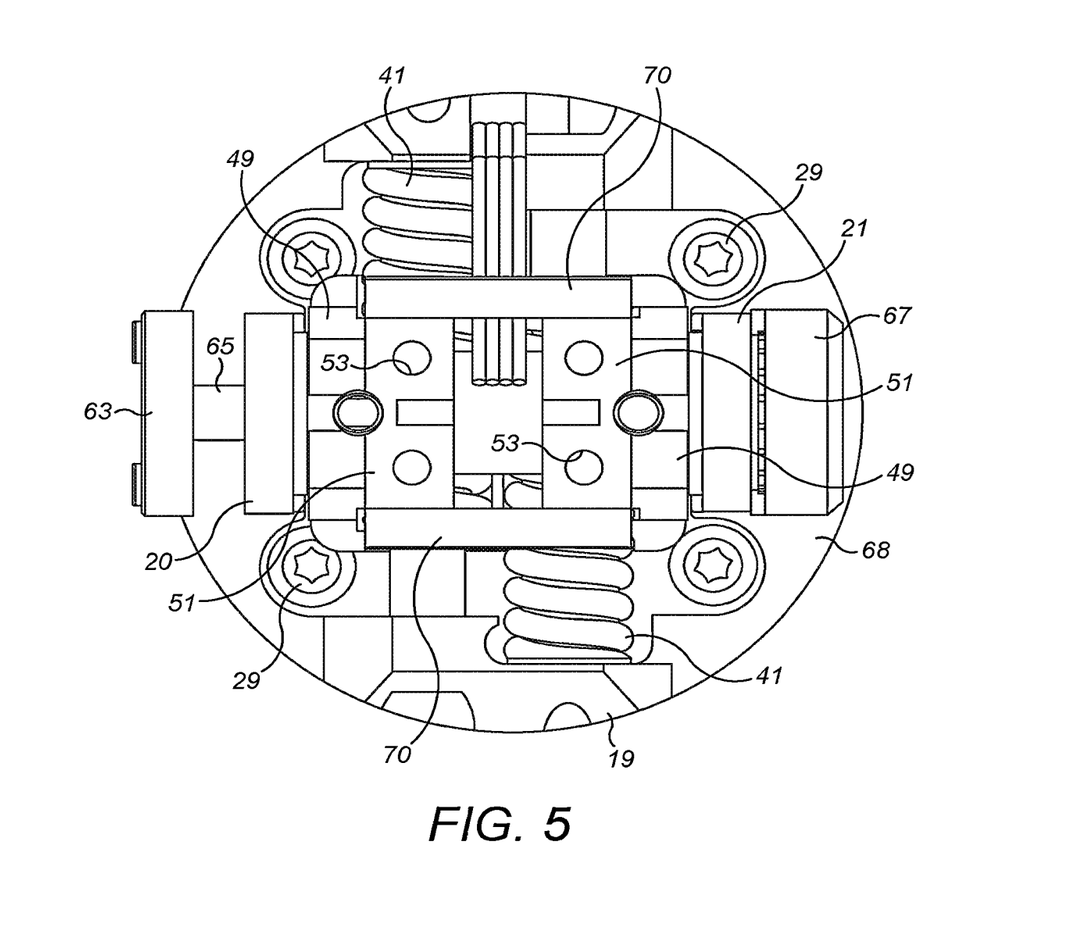

The components which permit the pivoting of the support plate, and also the components which make up the aforementioned locking mechanism, can be viewed in FIGS. 2, 4 and 5. A generally circular mount 19 forming a part of the base 3 is provided, the mount 19 having a pair of upwardly extending lugs 20,21 on opposing sides of the mount 19. Each lug 20,21 includes an aperture 23 through which, in use, the pivot axis A extends. A cover plate 25 is provided between the mount 19 and base 3 in order to cover the base. One or more shims 27 may be provided on an upper surface 68 of the mount 19 so as to adjust the height of that upper surface 68, the reasons for which will be explained in more detail below. The mount 19 is attached to the base 3 by a plurality of threaded screws 29.

Each lug 20,21 is provided with a pair of openings 31 which extend through the lug 21 below its respective aperture 23. Alternatively, each lug 20,21 may be provided with a pair of recesses which open on the outer faces of the lugs 20,21. In other words the recesses open on the faces of the lugs 20,21 which face away from one another. A mount magnet 33 is fixed into each opening 31 or recess using glue or a similar bonding agent, so that the mount magnets 33 are exposed at least on the outer faces of the lugs 20,21.

A rack 35 is located on the base 3 within a central opening 28 in the mount 19. Both the rack 35 and opening 28 are generally square or rectangular in shape, but the opening 28 is wider than the rack 35 in a direction substantially transverse to the pivot axis A so that the rack 35 may slide transversely within the opening 28 along an axis which is substantially perpendicular to the pivot axis A. The rack 35 includes a pair of hemi-cylindrical recesses 37 which extend in the transverse direction relative to axis A. Each end of the rack 35 is provided with a plurality of upwardly extending teeth 39 which run along the ends of the rack in the transverse direction.

A biasing means in the form of a compression spring 41 is located in each of the hemi-cylindrical recesses 37 in the rack 35. Each recess 37 is open on one side of the rack 35 and is closed on the opposing side of the rack 35, with the two recesses 37 open on opposing sides of the rack 35. As a result, one end of each spring 41 lies against an internal surface of the rack 35 defined by the closed end of its respective recess 37 and, when the rack 35 is located in the opening 28, the other end of each spring 41 lies against a surface of the mount 19 adjacent the opening 28. Stop washers 43 are placed in the opposing ends of each spring 41 to assist with the engagement of the springs 41 with their respective surfaces. With this arrangement, the springs 41 hold the rack 35 in equilibrium within the opening 28 in the mount 19, with the biasing forces created by the springs 41 pushing in substantially opposite directions and being substantially equal and balanced. Fine tuning of the biasing forces and balance of the rack 35 can be undertaken by way of first and second adjustment screws 45 which extend through either side of the mount 19 and engage an end of their respective first and second springs 41.

FIG. 2 also illustrates the components of the device 1 which provide the pivoting arrangement and the locking mechanism. A pinion 47 is provided which has a gear element 49 at either end thereof. Adjacent each gear element 49 is an upwardly facing mounting surface 51 to which the support plate (not shown in FIG. 2) is fixed via a pair of threaded apertures 53 in each mounting surface 51. A bore 55 extends longitudinally through the pinion 47 and in use the pivot axis A will extend through the bore 55. Each gear element 49 has a plurality of downwardly projecting gear teeth 50 which in use engage with the upwardly projecting teeth 39 of the rack 35. Consequently, when the device 1 is assembled rotation of the pinion 47 about pivot axis A will result in a linear motion of the rack 35 perpendicular to the axis A within its opening 28 in the mount 19.

During assembly of the device, the pinion 47 is placed between the first and second mount lugs 20,21 and a pinion shaft 57 is extended through the lug apertures 23 and pinion bore 55. Bearings 59 are located on the shaft 57 between each end of the pinion 47 and its respective lug 20,21. A pair of grub screws 61 connect the pinion 47 to the pinion shaft 57 via apertures in both components so that they rotate as one element.

The pinion shaft 57 is hollow and includes a locking element in the form of a toothed wheel 58 attached to one end thereof such that when the shaft 57 is in position the toothed wheel 58 is located outside the second mount lug 21. A first actuator button 63 is provided which has an actuator shaft 65 attached to it. During assembly, the first button 63 and the actuator shaft 65 are brought in from outside the first mounting lug 20 and the shaft 65 is fed through the aperture 23 in the first lug 20, the pinion shaft 57 and the aperture 23 in the second lug 21 so that the free end of the actuator shaft 65 projects from the toothed wheel 58 end of the pinion shaft 57. A second actuator button 67 is then connected to the free end of the actuator shaft 65. As a result, the first and second actuator buttons 63,67 and the actuator shaft 65 running between them can now slide as an actuator axially along the pivot axis A relative to the pinion 47, pinion shaft 57 and mount 19. Both the first and second actuator buttons 63,67 have flat bottom surfaces 64,66 which engage with an upper surface 68 of the mount 19 whenever one of the buttons 63,67 is pushed inwards towards the mount 19, thereby preventing rotation of the buttons 63,67 and actuator shaft 65 relative to the mount 19.

Axial movement of the actuator arrangement is limited by the buttons 63,67 coming into contact with the outer faces of the first and second mount lugs 20,21. Although not visible in FIG. 2, the inner face of the second actuator button 67 has a locking element in the form of a toothed recess which corresponds to the general shape of the toothed wheel 58 on the end of the pinion shaft 57. Either the teeth of the toothed wheel 58 or those of the toothed recess may have chamfered leading edges to assist with the engagement of the wheel 58 and recess when axial movement of the actuator brings the second actuator button 67 into contact with the toothed wheel 58. When the second button 67 is pressed as far as possible in towards the mount 19, the toothed wheel 58 will locate in the locking recess of the second button 67 and rotational motion of the pinion 47 and pinion shaft 57 relative to the buttons 63,67 will be prevented. Furthermore, as the flat bottom surface 66 of the second button 67 will be engaged with the upper surface 68 of the mount 19, rotation of the actuator buttons 63,67 and their shaft relative to the mount 19 is also prevented so the rack and pinion arrangement will be locked in its present position.

Button magnets 69 are located in recesses or openings in the buttons 63,67 so that the magnets 69 are partially exposed on at least the inner surfaces of each button 63,67. In other words, the magnets 69 are partially exposed on the surfaces of the buttons 63,67 which will come into contact with the mount lugs 20,21. The magnets 69 in the first and second buttons 63,67 and the mount magnets 33 fixed in the mount lugs 20,21 attract one another so as to assist in sliding the buttons 63,67 towards and away from the locking position.

Once assembly has been completed of the aforementioned components, the cover member 17 can be placed over the sliding lock mechanism in order to make it as easy as possible for a wearer to operate the lock. The underside of the cover member 17 is provided with a pair of slots 18, one of which is visible through an opening 16 in the cover 17 in FIG. 2. These slots 18 receive the actuator buttons 63,67 in a snap fitting such that the cover 17 is then detachably secured to the locking mechanism, and axial movement of the cover 17 along the pivot axis A will move the actuator in and out of the locking position.

Figure 3:
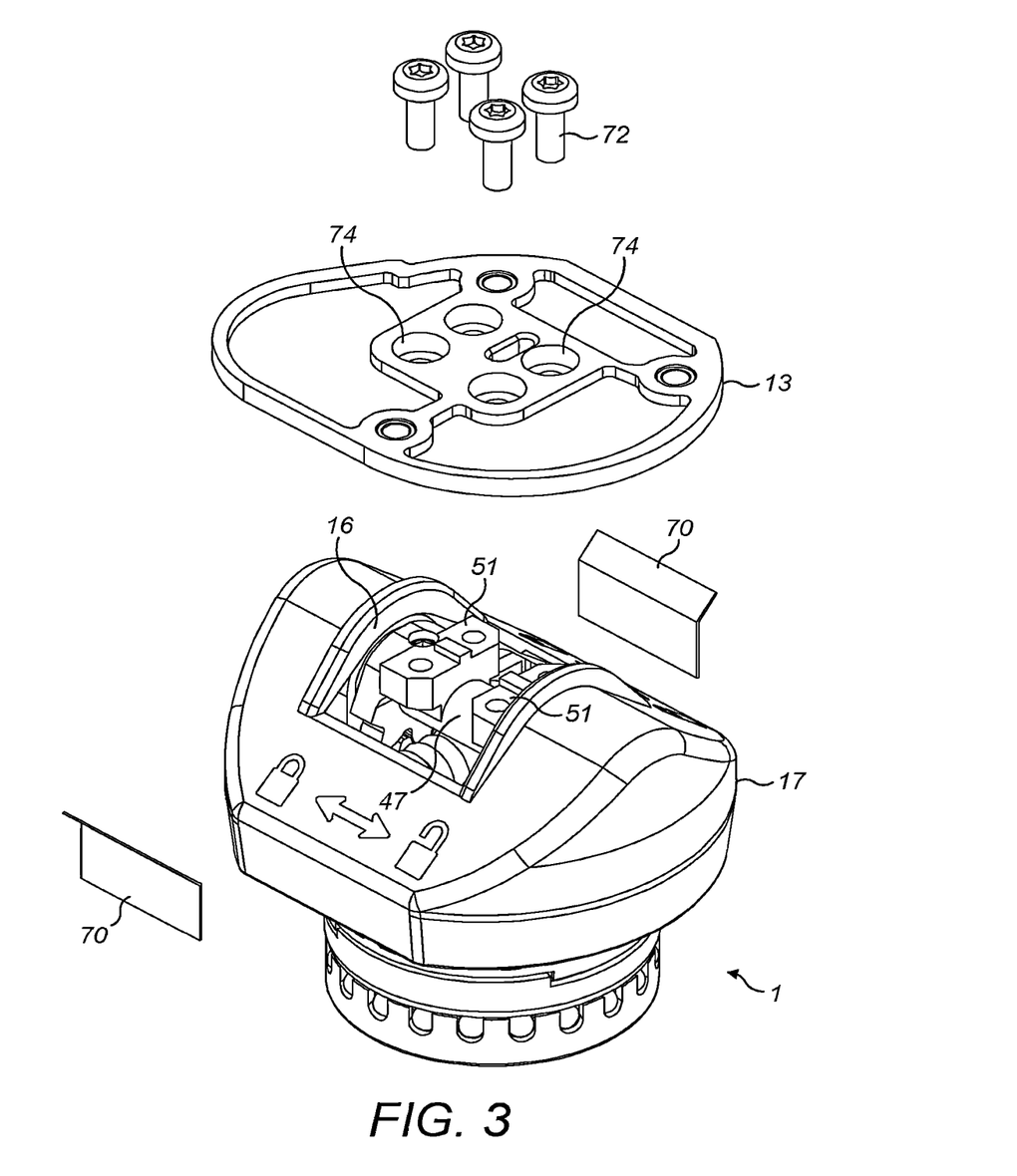
FIG. 3 is a perspective view of the wrist device of FIGS. 1 and 2 when partly assembled.

With the cover 17 attached to the locking mechanism the device 1 will appear as shown in FIG. 3. A pair of flexible coverings 70 are placed either side of the opening 16 in the cover 17 so that the coverings 70 lie between the cover 17 and the components of the device contained therein. The support plate 13 can then be attached to the mounting surfaces 51 on the pinion 47 via screws 72 extending through the corresponding apertures 74 in the support plate 13. With the support plate 13 attached to the pinion 47, the coverings 70 protect the inner workings of the device from the ingress of dirt and other contaminants through the cover opening 16, and also improve the appearance of the device with the majority of the components hidden.

To operate the device, the wearer can lock or unlock the device either by manipulating the cover 17 with their other hand, or else by gently knocking one end of the cover against a surface. The magnets 33, 69 in the mount lugs 20,21 and actuator buttons 63,67 assist in moving the device between the locked and unlocked positions as they draw the actuator buttons 63,67 towards their respective lugs 20,21 when they come within a certain distance of the lugs 20,21. The magnets also provide a sufficient attraction force that the cover cannot be moved out of its present position without a reasonable force being applied to the cover. This is especially beneficial when the device is locked in a given position, so that the chances of the device being accidentally unlocked are reduced.

When in the unlocked position, the pinion 47 and support plate 13 are free to rotate about the pivot axis A relative to the base 3. At the same time, the springs 41 provide a damping force such that any forces applied to a hand attached to the plate 13 such as, for example, caused by the hand accidentally knocking against a surface, are not transmitted through the device to the socket and residual limb of the wearer. Furthermore, the springs 41 provide balanced biasing forces either side of the rack 35 which will return the plate 13 and limb attached thereto to a neutral position when the device is unlocked and no forces are being applied to the hand. The neutral position is a rest or zero position assumed by the rack 35 and plate 13 when no external forces other than those of the biasing springs 41 are being applied.

When the wearer wishes to place their prosthetic hand in a given position in the flexion/extension plane, they first manipulate the hand into the desired position using their other hand or by pressing the hand against a surface in order to overcome the biasing forces of the springs 41. Then, whilst maintaining the desired position of the hand, they then move the cover 17 towards the locked position. As described above, moving the cover 17 to the locked position brings the recess in the second actuator button 67 into contact with the toothed wheel 58 on the end of the pinion shaft 57 and also brings the bottom surface 66 of the button 67 into contact with the upper surface 68 of the mount. Thus, the button 67 cannot itself rotate and also holds the pinion shaft against rotation at the same time. One or more of the shims 27 can be placed upon the upper surface 68 of the mount in order to eradicate play or backlash between the teeth of the toothed wheel 58 and corresponding toothed recess in the second actuator button 67.

FIGS. 4 and 5 show the fully assembled device in the locked position, with the support plate and cover removed for illustrative purposes.

The wrist device of the present invention provides a damping arrangement in which the support plate and limb attached thereto biased towards a rest or neutral position. As the biasing forces applied are balanced the wearer does not need to apply a large force to the limb in order to overcome those biasing forces. The wearer will therefore not experience as much fatigue using this device as is caused by repeated movements of the prior art devices such as those described in the introduction to this specification. Furthermore, partially locating the biasing means within the rack allows the device to be more compact than known wrist arrangements.

The locking mechanism of the present invention provides a linear actuator which can be shuttled between locked and unlocked positions simply by the wearer pressing on a given end of the actuator, or indeed by pressing one end of the actuator against a surface. No biasing forces need to be overcome by the wearer in order to unlock the device, again limiting the fatigue which a wearer will encounter from repeatedly moving and locking the device in different positions. When present, magnets placed in at least one of the base member and actuator ensure that the actuator cannot be moved from the locked position without a predetermined force being applied to the actuator, but also assist the wearer in sliding the actuator into the desired position.

Although the preferred embodiment of the device incorporates a pair of biasing members, the balanced biasing force applied to the rack may alternatively be provided by way of a single biasing member (e.g. a coil spring) connected between the base and rack and arranged so movement of the rack in either direction perpendicular to the pivot axis will be resisted by the biasing member. Furthermore, whilst springs such as compression springs are the preferred biasing members, alternative biasing members such as resilient elastomer rods, for example, may be used instead.

Whilst the biasing members are preferably partially located in the rack for compactness of the device, they may be placed outside the rack and apply their forces in opposing directions to outer surfaces of the rack.

The locking mechanism may comprise an actuator with a single button for sliding the actuator into a locking position. Such an actuator may have a single locking element which engages the pinion to prevent rotational motion thereof. The pinion need not have a pinion shaft, but instead may be rotatably supported by bearings directly on the actuator shaft.

Whilst magnets are preferably provided on each of the base member and actuator, the device may only have one or more magnets on one of the base member and actuator.

The device may be provided without a cover member, wherein operation of the actuator would be achieved by directly pressing the actuator buttons on either end of the actuator.

The base member may be provided with an alternative arrangement for connecting the base to the wearer. For example, the base may be provided with a bayonet fitting which would engage with a corresponding fitment on a socket worn by the user.

Whilst the preferred embodiment of the present invention describes the use of the device with a prosthetic hand, it should be understood that the invention may also be used with other prosthetic limbs. For example, the device may support a limb comprised simply of one or more digits on a support chassis rather than a complete hand.

These and other modifications and improvements may be incorporated without departing from the scope of the invention.

The invention claimed is:

1. A method of using a wrist device for a prosthetic limb, the method comprising:
   rotating a prosthetic hand, that is attached to the wrist device, about a pivot axis to a first position;
   countering a biasing force of a biasing member in the wrist device;
   depressing a button of the wrist device; and
   moving an actuator in the wrist device axially along the pivot axis in a first direction, thereby locking the wrist device with the prosthetic hand in the first position, wherein locking the wrist device with the prosthetic hand in the first position comprises bringing a recess in the actuator into contact with a toothed wheel on an end of a pinion shaft.

2. The method of claim 1, wherein rotating the prosthetic hand attached to the wrist device to the first position comprises using another hand to position the prosthetic hand or pressing the prosthetic hand against a surface.

3. The method of claim 1, wherein locking the wrist device with the prosthetic hand in the first position comprises bringing a bottom surface of the actuator into contact with an upper surface of a base of the wrist device.

4. The method of claim 1, further comprising moving the actuator in the wrist device axially along the pivot axis in a second direction opposite the first direction, thereby unlocking the wrist device with the prosthetic hand.

5. The method of claim 4, further comprising rotating the prosthetic hand to a second position different from the first position.

6. The method of claim 5, further comprising again moving the actuator in the wrist device axially along the pivot axis in the first direction, thereby locking the wrist device with the prosthetic hand in the second position.

7. The method of claim 1, wherein moving the actuator comprises linearly moving an actuator shaft.

8. The method of claim 1, wherein the biasing member comprises a spring.

9. The method of claim 1, further comprising rotating a pinion in response to rotating the prosthetic hand.

10. The method of claim 9, further comprising linearly moving a rack in response to rotating the pinion.

11. The method of claim 1, further comprising applying a magnetic force to the actuator to assist with moving the actuator in the first direction.

12. A method of using a wrist device for a prosthetic limb, the method comprising:
   translating an actuator in the wrist device axially along a pivot axis in a first direction, thereby rotationally unlocking a prosthetic hand that is rotationally attached to the wrist device in a first position;
   rotating the prosthetic hand about the pivot axis from the first position to a second position;
   rotating a pinion in response to rotating the prosthetic hand;
   linearly moving a rack in response to rotating the pinion;
   applying a biasing force opposing the linear movement of the rack; and translating the actuator in the wrist device axially along the pivot axis in a second direction opposite the first direction, thereby locking the prosthetic hand that is rotationally attached to the wrist device in the second position.

13. The method of claim 12, wherein translating the actuator in the first direction comprises depressing a button in the first direction.

14. The method of claim 12, wherein translating the actuator in the second direction comprises depressing a second button in the second direction.

15. The method of claim 12, further comprising tuning the biasing force via an adjustment screw.

16. The method of claim 12, further comprising:
translating the actuator in the first direction again, thereby rotationally unlocking the prosthetic hand from the first position; and
providing balanced biasing forces to opposite sides of the rack to thereby cause the prosthetic hand to rotate to a neutral position.

17. The method of claim 12, wherein rotating the prosthetic hand comprises rotating a support plate that couples the actuator to the prosthetic hand.

18. The method of claim 12, further comprising applying a magnetic force to the actuator to assist with moving the actuator in the first direction.

19. The method of claim 12, wherein translating the actuator comprises translating an actuator shaft.

20. A method of using a wrist device for a prosthetic limb, the method comprising:
rotating a prosthetic hand, that is attached to the wrist device, about a pivot axis to a first position;
countering a biasing force of a biasing member in the wrist device;
depressing a button of the wrist device; and
moving an actuator in the wrist device axially along the pivot axis in a first direction, thereby locking the wrist device with the prosthetic hand in the first position, wherein moving the actuator comprises linearly moving an actuator shaft.

21. A method of using a wrist device for a prosthetic limb, the method comprising:
rotating a prosthetic hand, that is attached to the wrist device, about a pivot axis to a first position;
rotating a pinion in response to rotating the prosthetic hand;
countering a biasing force of a biasing member in the wrist device;
depressing a button of the wrist device; and
moving an actuator in the wrist device axially along the pivot axis in a first direction, thereby locking the wrist device with the prosthetic hand in the first position.

22. The method of claim 21, further comprising linearly moving a rack in response to rotating the pinion.

23. A method of using a wrist device for a prosthetic limb, the method comprising:
rotating a prosthetic hand, that is attached to the wrist device, about a pivot axis to a first position;
countering a biasing force of a biasing member in the wrist device;
depressing a button of the wrist device;
moving an actuator in the wrist device axially along the pivot axis in a first direction, thereby locking the wrist device with the prosthetic hand in the first position; and
applying a magnetic force to the actuator to assist with moving the actuator in the first direction.

* * * * *